(12) United States Patent
Greff

(10) Patent No.: US 9,962,402 B2
(45) Date of Patent: May 8, 2018

(54) HEALING COMPOSITION FOR TOPICAL APPLICATION

(75) Inventor: Daniel Greff, Mere (FR)

(73) Assignee: BIOPASS S.A., Luxembourg (LU)

( * ) Notice: Subject to any disclaimer, the term of this patent is extended or adjusted under 35 U.S.C. 154(b) by 0 days. days.

(21) Appl. No.: 14/006,052

(22) PCT Filed: Apr. 5, 2012

(86) PCT No.: PCT/FR2012/050735
§ 371 (c)(1),
(2), (4) Date: Sep. 24, 2013

(87) PCT Pub. No.: WO2012/136934
PCT Pub. Date: Oct. 11, 2012

(65) Prior Publication Data
US 2014/0044667 A1    Feb. 13, 2014

(30) Foreign Application Priority Data
Apr. 6, 2011 (FR) ...................................... 11 52997

(51) Int. Cl.
| | | |
|---|---|---|
| *A61K 31/78* | (2006.01) | |
| *A61K 8/04* | (2006.01) | |
| *A61K 8/34* | (2006.01) | |
| *A61K 8/81* | (2006.01) | |
| *A61K 9/00* | (2006.01) | |
| *A61Q 19/00* | (2006.01) | |
| *A61K 8/86* | (2006.01) | |
| *A61K 45/06* | (2006.01) | |
| *A61K 8/39* | (2006.01) | |
| *A61K 9/06* | (2006.01) | |

(52) U.S. Cl.
CPC ............. *A61K 31/78* (2013.01); *A61K 8/042* (2013.01); *A61K 8/345* (2013.01); *A61K 8/39* (2013.01); *A61K 8/8152* (2013.01); *A61K 8/86* (2013.01); *A61K 9/006* (2013.01); *A61K 9/0014* (2013.01); *A61K 9/0031* (2013.01); *A61K 9/0043* (2013.01); *A61K 9/0046* (2013.01); *A61K 45/06* (2013.01); *A61Q 19/002* (2013.01); *A61Q 19/005* (2013.01); *A61K 9/06* (2013.01)

(58) Field of Classification Search
CPC ........ A61Q 19/00; A61Q 19/08; A61Q 17/04; A61Q 19/005; A61Q 17/005; A61Q 19/007; A61Q 19/008; A61Q 1/04; A61K 8/975; A61K 8/64; A61K 2800/31; A61K 47/10; A61K 8/34; A61K 8/498; A61K 8/97; A61K 9/0014
See application file for complete search history.

(56) References Cited

U.S. PATENT DOCUMENTS

| | | | | |
|---|---|---|---|---|
| 4,885,161 A | * | 12/1989 | Cornell | ............... A61L 26/0052 |
| | | | | 424/447 |
| 2013/0211309 A1 | * | 8/2013 | Inamoto | .................. A61L 15/26 |
| | | | | 602/48 |

FOREIGN PATENT DOCUMENTS

| | | | | |
|---|---|---|---|---|
| EP | 1206933 A1 | * | 5/2002 | ............... A61K 7/48 |
| EP | 1 238 651 A1 | | 9/2002 | |
| EP | 1 543 825 A1 | | 6/2005 | |
| FR | 2 682 296 A1 | | 4/1993 | |
| FR | 2 737 406 A1 | | 2/1997 | |
| FR | 2 787 709 A1 | | 6/2000 | |
| FR | 2 854 897 A1 | | 11/2004 | |
| JP | 2010-120859 A | | 6/2010 | |
| WO | WO 97/30692 A1 | | 8/1987 | |
| WO | WO97/47310 | * | 6/1996 | |
| WO | WO 97/05856 A1 | | 2/1997 | |
| WO | WO 97/47310 A1 | | 12/1997 | |

OTHER PUBLICATIONS

International Search Report issued in PCT/FR2012/050735, dated Oct. 22, 2012, 7 pages.
Written Opinion issued in PCT/FR2012/050735, 8 pages.

* cited by examiner

*Primary Examiner* — Nannette Holloman
(74) *Attorney, Agent, or Firm* — Arent Fox LLP

(57) ABSTRACT

The present invention relates to a hygiene product or a pharmaceutical composition in the form of a gel or dressing, for topical application to the skin or mucosa including glycerol, at least one poly(meth)acrylate polymer, at least one polyethylene glycol having a molecular weight of less than 1000 g/mol, octanediol and water.
The composition or dressing can be used for healing treatment of chronic dermal ulcers, healing and soothing treatment of eczema and psoriatic conditions, healing treatment of anal fissures, treatment of mouth injuries, resorption and healing of labial herpes (cold sore) and treatment of dermatitis.
The hygiene product can be a shaving or aftershave product for sensitive or hypersensitive skin, a nasal decongestant product or a product for ear hygiene.

5 Claims, No Drawings

HEALING COMPOSITION FOR TOPICAL APPLICATION

CROSS REFERENCE TO RELATED APPLICATIONS

This application is a National Stage entry of the International Patent Application No. PCT/FR2012/050735, filed Apr. 5, 2012 which claims priority to French Patent Application No. 1152997, filed Apr. 6, 2011. The disclosures of the prior applications are hereby incorporated in its entirety by reference.

The invention relates to a composition for topical application, in particular a dermatological or pharmaceutical composition in the form of a hydrogel exhibiting healing properties. The composition of the invention is particularly effective in the management of acute skin lesions—such as wounds—and chronic skin lesions, such as ulcers and cicatrices.

The skin consists of the dermis and the epidermis. The epidermis carries out, by virtue of its structure, the impervious barrier function of the body in relation to the outer world. The epidermis is organized into various layers, the basal layer, the prickle cell layer (stratum spinosum), the granular layer (stratum granulosum), the stratum lucidum and the horny layer (stratum corneum). The expression acute skin lesion for the purposes of the invention is understood to mean the destruction of all or part of the skin covering occurring following a trauma, whether involving accidental or surgical wounds, cuts, or lesions from rubbing (avulsions). The lesion may be extensive to a greater or lesser degree and may be deep to a greater or lesser degree, depending on whether it affects a wide area of the skin or not.

STATE OF THE ART

Patent applications FR 2 737 406 and WO 97/30692, and WO 97/05856 describe aqueous gels combining diols, polyacrylate polymers and glycerine. These gels exhibit a particularly high antimicrobial activity and are proposed as substitutes for preservatives in pharmaceutical, cosmetic and dermatological products. These documents do not describe any biological property which these gels may have on the skin. They are simply used as a preservative in finished products.

Application WO 97/474310 describes, for its part, anti-inflammatory and moisturizing properties of some of these gels. For example, a gel consisting of 1% by weight of polyacrylate, 34% by weight of water and 65% by weight of glycerine is effective in the prevention of an erythema and of dry skin which may appear following radiotherapy sessions. Their use in the prevention of mild burns, that is to say not open, which are also termed first degree or mild second degree burns, is suggested on the basis of their antiseptic and moisturizing power.

Most of the examples of formulation which are given in this document contain ethoxydiglycol. Now, it has been discovered in the context of the present invention that this compound significantly slows wound healing. Its presence in a gel therefore prevents the treatment from succeeding on a skin a portion of whose epidermis or dermis has been destroyed.

Moreover, some products which have been developed by following the teachings of the document WO 97/474310 have proved, on the basis of clinical studies, unsuitable for the care of severe burns (such as deep second degree burns or third degree burns), superinfected burns or abraded skins. Accordingly, contrary to the suggestions of this document, none of the gels which it describes is suitable for the treatment of acute or chronic skin lesions.

It has also been described that gels based on polyacrylate, water and glycerine are endowed with moisturizing properties for the top layers of the skin and may be used in care lines for sensitive skins or for dry skins. For example, most of the examples of formulation given in the document WO 97/474310 contain high proportions of glycerine. One embodiment presented as being preferred is composed of 30-60% glycerine, 30-50% water and 0.1-5% polymer. The moisturizing properties of these gels are derived from the high proportion of glycerine which they contain. Indeed, glycerine is a small molecule capable of penetrating into the superficial cells of the epidermis, of capturing at least some of the water present in the cosmetic or pharmaceutical composition, and of retaining it in the cells by virtue of its hygroscopic properties. Polyacrylate and glycerine gels are therefore known for their moisturizing properties on the surface of healthy skin.

AIMS OF THE INVENTION

The main aim of the invention is to solve the technical problem consisting in providing a healing pharmaceutical composition for the topical care of acute or chronic skin lesions, and of mucosal lesions.

The aim of the invention is to provide pharmaceutical compositions ensuring a particularly effective healing of wounds on the skin or the mucosa. The aim of the present invention is in particular to provide a composition whose healing activity is at least comparable, or even enhanced, compared with healing compositions of the prior art.

The aim of the invention is also to provide such compositions in a reproducible manner on an industrial scale, which are inexpensive and reliable from the point of view of their topical acceptance on the skin and the mucosa.

DESCRIPTION OF THE INVENTION

It has been discovered that the compositions of the present invention have particularly advantageous healing properties extending beyond the properties hoped for. The composition of the invention allows healing that is at least equal, or even superior, to that of some reference compositions of the prior art.

Healing for the purposes of the invention includes the processes by which the skin or the mucosa closes and repairs any discontinuity in its structure after an attack which leads to a deep (as opposed to a superficial) lesion. These attacks include, for example, a cut, a voluntary opening made for a surgical operation, or skin ulcers. Deep lesions are distinguishable from superficial lesions which only affect the epidermis. The progression and disturbances of deep lesions pose delicate therapeutic problems which do not exist with superficial lesions.

Healing comprises four stages including blood clotting, inflammatory swelling, cleansing with detergent, and finally the proliferation of new tissues which allows, according to the cases, joining of the edges of the wound or granulation which reconstructs the epithelium. This mechanism results in the formation of a cicatrix whose esthetic quality is high to a greater or lesser degree, depending on the depth and the width of the initial lesion.

In the case of deep lesions, healing corresponds to a complex mechanism: after the immediate inflammatory reaction, the compensation for the loss of substance is obtained by a young and loose temporary tissue, the fleshy granulation or granulation tissue. This tissue contains numerous macrophages and fibroblasts which secrete various components of the extracellular matrix (glycosaminoglycans, fibronectin and collagen). A large capillary vascular network develops within this granulation tissue. Certain fibroblasts, the myofibroblasts, exhibit characteristics comparable to those of the smooth muscle cells and are capable of contraction. They are responsible for a retraction of the edges which help to close the wound. When the granulation has compensated for the loss of substance, epidermal repair occurs either from the edges of the lesion or from the healthy epidermal leftovers in the wound. After transverse migration resulting in the closure of the wound, a vertical proliferation with differentiation and maturation of the keratinocytes into a pluristratified epithelium is observed followed by the reconstruction of the various types of cells of the epidermis.

Once the wound has been closed, secondary progression is long and variable before reaching cicatricial maturation from which the cicatrix is no longer inflammatory and no longer progresses. It is quite clear how the mechanism of healing of superficial wounds differs from the mechanism of healing of deep wounds. The means for treating them cannot therefore be identical.

During the entire phase preceding cicatricial maturation, persistence of inflammation of the dermis with hypervascularization and edema, anarchic and nonoriented deposition of collagen III, presence of myofibroblasts and deposits of fibrous tissue is observed. The fibrous tissue and collagen deposits can considerably thicken the dermis and leave hypertrophic cicatrices; sometimes these deposits lead to true skin tumors, the keloids.

Improvement in the healing of wounds provided by the compositions of the present invention may result in an acceleration of healing: the delay in complete healing is reduced. It may also result in a reduction in the pain which the wounds can cause during healing. This result is all the more surprising since the prior art has only mentioned the moisturizing properties of glycerine and polyacrylate gels on the superficial layers of the skin.

The compositions of the invention also advantageously make it possible to avoid or to limit the formation of cicatrices and of inesthetic achromic spots which can remain after complete healing of the wound.

The compositions of the invention allow in particular better epithelialization of the lesion and a significant reduction in the size of the lesion. They increase the degree of epithelialization of deep lesions. They also allow re-epithelialization of chronic skin ulcers which could no longer be naturally operated on.

It has been discovered, quite unexpectedly, that particular polyacrylate and glycerine gels make it possible to promote healing of wounds or of skin lesions—chronic or acute—which are deep to a greater or lesser degree and for which the epidermis has been practically destroyed.

The composition of the invention advantageously makes it possible to heal a chronic or acute wound more rapidly, while minimizing the suffering of the patient and while avoiding cicatricial complications. This objective is achieved for the first time with a topical therapeutic.

Composition

Accordingly, the present invention relates to a pharmaceutical composition for topical application to the skin or the mucosa containing less than 0.1% by weight of ethoxydiglycol and comprising water, from 5 to 25% by weight of glycerol, from 0.01 to 2% by weight of at least one poly (meth)acrylate polymer, from 0.5 to 5% by weight of at least one polyethylene glycol having a molecular mass of less than 1000 g/mol, from 0.1 to 1.5% by weight of octanediol, the percentages by weight being expressed relative to the total weight of the composition.

The composition advantageously comprises from 5 to 25% by weight of glycerol (also called glycerine), preferably from 5 to 20% by weight, and more preferably from 5 to 10% by weight of glycerol relative to the total weight of the composition.

The composition advantageously comprises from 0.5 to 5% by weight of polyethylene glycol, preferably from 1 to 5% by weight, and more preferably from 2 to 4% by weight of polyethylene glycol relative to the total weight of the composition. The molecular mass by weight of polyethylene glycol is advantageously less than 1000 g/mol, preferably between 200 and 600 g/mol, for example of the order of 400 g/mol.

A polyethylene glycol is preferably of low molecular weight, preferably chosen from polyethylenes having a molecular mass of less than 500 g/mol, such as PEG-8 (also called octaethylene glycol). It is also possible to use polyethylene glycols with the common name PEG 200, PEG 400, PEG 600 or PEG 1000 (in which the number corresponds to a weight-average molecular mass).

The poly(meth)acrylate polymer is for example present in the composition in a quantity of 0.1 to 2% by weight relative to the total weight of the composition.

As poly(meth)acrylate polymer, use is preferably made of a polymer in the form of a salt, and preferably a salt of an alkali metal such as sodium or potassium salts. As poly (meth)acrylate, use is made for example of a product from the Carbopol® range from the company Goodrich. It is possible to advantageously use a mixture of several poly (meth)acrylates, such as the mixture of a methyl polymethacrylate, of crosslinked acrylate/C10-30 alkyl acrylate polymer (INCI name Carbomer) and of sodium polyacrylate.

The composition preferably comprises from 0.1 to 1.5% by weight of octanediol, preferably from 0.5 to 1.5% by weight relative to the total weight of the composition. The mass ratio between glycerine and octanediol is preferably between 5:1 and 15:1, and preferably still between 8:1 and 10:1.

A preferred octanediol is 1,2 octanediol, also called caprylyl glycol.

According to a particular embodiment, the composition of the present invention consists of the combination of glycerol, of at least one poly(meth)acrylate polymer, of at least one polyethylene glycol having a molecular weight of less than 1000 g/mol, of octanediol, of water, and optionally of an ingredient which is active on the healing of the skin known to a person skilled in the art. The characteristics which have been described above, in particular the contents of the various components of the composition, all apply to this particular embodiment.

The composition of the present invention contains less than 0.1% by weight of ethoxydiglycol, and preferably does not contain any of it, because it has been discovered in the context of the present invention that this compound interferes with the biological processes of the skin. It in particular significantly delays wound healing. Its presence in the composition therefore prevents the treatment from succeeding.

The concentrations of the products of the composition of the present invention are stated according to the final formulation which depends on the desired application.

The composition of the present invention is preferably in the form of a gel or a hydrogel.

A composition in the form of a hydrogel according to the invention having a particularly advantageous composition comprises water, from 5 to 25% by weight of glycerol; from 0.01 to 2% by weight of poly(meth)acrylate; from 0.5 to 5% by weight of polyethylene glycol and from 0.1 to 1.5% by weight of 1,2-octanediol, relative to the total weight of the composition.

According to one variant, the composition of the invention solely consists of glycerol; of at least one poly(meth)acrylate polymer; of at least one polyethylene glycol having a molecular weight of less than 1000 g/mol; of at least one octanediol; and of water.

In one embodiment, the composition of the invention consists of water, from 5 to 25% by weight, preferably from 5 to 10% by weight, of glycerol; from 0.01 to 2% by weight of poly(meth)acrylate; from 0.5 to 5% by weight, preferably from 1 to 5% by weight, of a polyethylene glycol, and from 0.1 to 1.5% by weight, preferably from 0.5 to 1.5% by weight, of 1,2-octanediol, the percentages being expressed relative to the total weight of the composition.

Treatments

It has been discovered—quite unexpectedly and contrary to the teaching of the prior art—that particular polyacrylate and glycerine gels make it possible to promote the healing of chronic and acute wounds or skin lesions. Among the chronic wounds, mention may be made of bedsores, ulcers, in particular diabetic foot ulcers. Among the acute wounds, mention may be made of deep second degree burns, third degree burns, skin abrasion, trauma wounds, and postoperative wounds.

Chronic or acute skin wounds for the purposes of the invention are deep lesions affecting the integrity of the structure of the skin or of the mucosa, beyond the granular layer, preferably up to the basal layer. Deep wounds generally affect the dermis over part or the whole of its thickness.

The composition of the invention is particularly useful for the treatment of lesions for which practically the whole of the epidermis has been destroyed. It is even effective on wounds for which the skin has been completely destroyed and which can only heal from the edges of the lesion or by carrying out a skin transplant.

In superficial wounds, such as superficial second degree burns, the loss of the stratum corneum and of its surface lipid film is responsible for the secondary death of numerous epidermal cells. Maintaining surface moisturization is sufficient to cure these wounds. That is not the case for more severe burns.

The compositions of the invention are advantageously used for the treatment of the skin wounds of diabetic persons and of elderly persons (over 60 years of age), in whom healing disorders are more frequent.

An ulcer for the purposes of the invention is a lesion of the skin or of the mucosa characterized by a loss of dermal substance. Ulcers can cause a complete loss of larger or smaller portions of epidermis and dermis and often even of subcutaneous fat.

For example, the composition of the invention is particularly effective for improving healing of ulcerated dermal blisters which may be caused by pathological conditions such as chicken pox or herpes. Blisters are large (greater than about 5 mm) skin lesions caused by a detachment between the various layers of the skin (epidermis, dermis, hypodermis). Blisters can become ulcerated or leave cicatrices; that is why it is essential to treat them. The composition of the invention is of most interest in the preventive or curative cicatrizing treatment of the healing of chicken pox and herpes spots, in particular of labial herpes.

Skin ulcers have the shape of open, often round or oval, craters. They present on their edges layers of skin which are eroded. The skin surrounding the ulcer may be reddened, swollen and sensitive or even painful. A liquid (mixture of lymph and some blood or pus sometimes) may ooze from the ulcer. The symptoms of chronic ulcer generally include increasing pain, a friable granular wound with rupturing of the wound instead of a cure. Ulcers which heal within 12 weeks or less are generally classed as "active", and those which heal more slowly are termed "chronic".

They are more frequent on the skin of the lower limbs but may also appear on the cheeks, the nose, the soft palette, the tongue, and inside the lower lip. These small mouth ulcers usually last from 7 to 14 days and can be painful.

The composition of the invention makes it possible to effectively treat ulcers, in particular chronic ulcers, by avoiding the infection of the ulcer, by limiting the loss of tissue by necrosis, by limiting oozing, by controlling edema, and by relieving the pain induced by lesions of the tissues and the nerves.

Among the ulcers, mention may be made of pressure ulcers. A lack of mobility (bed confinement, wheelchair) causes prolonged pressure on certain tissues, which limits blood and lymphatic circulation, which promotes skin ulcers commonly called bedsores.

Ulceration of wounds is more frequent on the lower limbs and the extremities of the body which are particularly vulnerable to circulatory disorders leading to one or more skin lesions and hindering their normal healing.

The compositions of the present invention are particularly effective for combating dermal ulcers, in particular chronic dermal ulcers located on the lower limbs.

It should be noted that a dermal ulcer, for example on the leg, is a loss of epidermal and dermal skin substance with a chronic progression in the absence of treatment. More than 90% of ulcers are of vascular origin. Venous etiology is the most frequent. The major problem is that of an absence of, or a particularly delicate, healing.

Venous ulcers occur during venous insufficiency of the lower limbs sometimes following phlebitis or varicose veins. Arterial leg ulcers occur in the event of an arterial circulatory disorder, for example after a following atherosclerosis. Venous ulcers represent 90% of leg ulcers and are generally (post thrombotic) varicose ulcers or are due to a chronic venous insufficiency (particularly in elderly or diabetic persons).

An ulcer may also occur following the stings or bites of animals capable of injecting a venom containing necrotizing toxins and enzymes. The composition of the invention is thus particularly useful for the treatment of the stings or bites of venomous animals such as wasps, bees, horseflies or jellyfish.

The composition of the invention also makes it possible to heal the wounds of the mucosa. The mucosa cover the walls of the digestive tube from the mouth to the anus, the walls of the respiratory apparatus such as the nostrils or the auditory canal, the walls of the vagina and the nipple of the breasts. The wounds of the buccal, labial and nasal mucosa are effectively healed using the composition of the invention.

The subject of the invention is also the composition described above for the healing treatment of anal fissures, the healing treatment of injuries to the buccal mucosa (such as aphthae or grazes caused by a denture), the healing treatment of the lips (in particular the healing treatment of labial herpes commonly called cold sore).

In the buccal mucosa, ulcers—commonly called aphthae—form on the inside of the lips and the cheeks, on the tongue, the palate, the gums or the throat. Injuries or irritations inside the mouth are generally caused by a poor adjustment of dental prostheses, by oral surgery, by an excessively energetic use of the toothbrush or by nibbling of the cheeks, which can cause the appearance of aphthae or the worsening thereof.

The composition may also be used for the healing of lesions which appear in the nostrils, in the event of a capillary rupture. As a prevention, it can advantageously serve as nasal decongestant or for ear hygiene.

The composition of the invention also makes it possible to manage the treatment of the cracks or fissures which frequently appear on the extremities of the body (heels of the feet, between the toes, fingers) or on the nipples of the breasts in the event of breastfeeding.

Permanent cicatrices are distinguishable from temporary cicatrices which only remain inflammatory and painful for a few days after the end of the healing process. The composition of the invention advantageously makes it possible to limit or prevent the maturation of the cicatrices into hypertrophic cicatrices or into keloids.

Advantageously, the composition of the present invention makes it possible to use other treatments chosen from the group consisting of:

the healing treatment of dermatitis, in particular of contact dermatitis of the hands, of seborrheic dermatitis of the face, dermatitis and itching of the scalp, the healing and soothing treatment of eczema and psoriatic conditions, and the healing treatment of diaper rash.

According to a particular embodiment, the composition of the invention is in the form of a gel packaged in a tube.

The composition may be applied to the skin and then covered with an occlusive dressing. It may also be applied on a gauze or a nonwoven which will have been placed on the wound beforehand.

According to a particular embodiment, the invention relates to an occlusive dressing comprising the composition of the invention.

The subject of the invention is also a ready to use dressing which does not require the putting in place of a gauze and a bandage, comprising in its structure the composition which has just been described. A dressing for the purposes of the invention comprises at least two layers, an inner layer intended to come into contact with the skin and a protective outer layer. The composition of the invention enters for example into the makeup of the inner layer. The outer layer of the dressing is generally a film or a foam made of a polymer material, for example made of polyurethane or of polyester/polyamide. The structure of the dressing may comprise a layer comprising a nonwoven, knitted or woven textile material, for example a compress.

As claimed in one embodiment, the composition or the dressing comprising it is applied to a wound caused by a surgical or dermatological operation, in particular in order to help the healing of the skin or of the mucosa.

The subject of the invention is also a hygiene product containing less than 0.1% by weight of ethoxydiglycol and comprising water, from 5 to 25% by weight of glycerol, from 0.01 to 2% by weight of at least one poly(meth)acrylate polymer, from 0.5 to 5% by weight of at least one polyethylene glycol having a molecular mass of less than 1000 g/mol, from 0.1 to 1.5% by weight of octanediol, the percentages by weight being expressed relative to the total weight of the composition. This hygiene product may be used as a shaving gel or as an aftershave balm for sensitive or hypersensitive skin, as a nasal decongestant, or for ear hygiene.

The hygiene product of the invention allows a good quality shaving, a practically immediate healing of the irritations caused by shaving and an antipain power for razor burn.

The present invention relates, according to another aspect, to a method of therapeutic treatment which consists in applying to a subject in need thereof, in particular a human being, a composition as described above to a lesion chosen from the group consisting of acute skin wounds, chronic skin wounds and lesions located on the mucosa.

This type of skin wound is distinguishable from more superficial wounds in which the dermis is not affected and only part of the epidermis has been damaged.

According to this method, the composition is applied to a cicatricial skin, a wound of the skin, in particular the skin of the face, the skin of the legs or the scalp.

The subject of the invention is also a method of treatment which consists in applying the composition described above to an area of ulcerated skin, in which the epidermis has been at least partially destroyed. As claimed in one embodiment, the composition may be used for the healing of a wound in which at least part of the dermis is damaged.

The subject of the invention is also a method of treatment which consists in applying the composition described above to an open wound or to a wound caused by a surgical operation.

All the characteristics which have been described above in relation to the composition of the invention apply to the method of treatment according to the invention as well.

Other aims, characteristics and advantages of the invention will appear clearly to a person skilled in the art after reading the following examples.

EXAMPLES

Example 1: Healing Treatment of Acute or Chronic Wounds

A single center prospective noncomparative clinical trial was carried out on volunteer patients suffering from various types of skin lesions. The average age was 60.3 years. The causes of the healing problems were mainly due to pressure ulcers (6 cases), foot cicatrices (7 cases), varicose ulcers (10 cases), deep second degree burns (2 cases), bullous dermatoses of the legs (3 cases), a fissure between the toes (2 cases) and a trauma ulcer (2 cases). The lower limbs were the main location (80%).

The composition which was applied was a hydrogel composed of water, of 0.5-1.5% by weight of 1,2-octanediol, of 5-10% by weight of glycerol, of 1-5% by weight of polyethylene glycol having a molecular mass of the order of 400 g/mol, of methyl polymethacrylate, of crosslinked acrylate/C10-30 alkyl acrylate polymer and of sodium polyacrylate.

The product was applied daily as a thick layer after having thoroughly cleaned the wound with physiological saline and having covered it with a sterile compress. The application of any other product to the studied area was avoided during the entire duration of the trial.

Evaluation Protocol:

The progression of the cicatrix was evaluated by iconography taken every week during the first 2 weeks, and then every month. It was evaluated by the patient and the doctor at the same time. The main final point was the level of re-epithelialization, the assessment of the efficacy and safety of the product (by the doctor) and the time for the disappearance of pain, oozing and erythema (by the doctor and the patient).

Results:

The results observed on a portion of the patients were not taken into account because of non compliance with the application.

The period for the disappearance of the erythema, of the pain and of the oozing was 1 week in 80% of the cases. The beginning of the cure was noted in the second week in 50% of the subjects. The treatment was applied for 3 months in 50% of the cases. The application was extended for more than 4 months in 4 cases. There was no side effect noted and the tolerance was judged to be good to very good in 100% of the cases.

Example 2: Evaluation of the Healing Efficacy on Lesions Post-Dermatological Procedure A comparative randomized study with the ointment HYALUZINC® was carried out. This study was performed on 2 groups of 22 volunteers having a lesion after a procedure with liquid nitrogen on keratoses or pigmented spots. The clinical signs are evaluated on D0, D12-D15 and D28 (in particular the reepithelialization of the lesion, the size of the lesion, the period for healing).

The composition of the invention was provided as a hydrogel composed of water, of 0.5-1.5% by weight of 1,2-octanediol, of 5-10% by weight of glycerol, of 1-5% by weight of polyethylene glycol having a molecular mass of the order of 400 g/mol, of methyl polymethacrylate, of crosslinked acrylate/alkyl C10-30 acrylate polymer and of sodium polyacrylate.

on D12-D15, the degree of reepithelialization of the lesion was 82% against 70% for the HYALUZINC® (positive control).

the softness of the skin was high or average in 90% of the subjects treated with the composition of the invention.

absence of residual cicatrix and of residual achromic spot in 100% of the subjects treated with the composition of the invention.

the period for complete healing of the lesion was 11 days for the composition of the invention and 13.2 days for the positive control.

These results demonstrate a healing activity that is at least comparable, or even greater than that of a reference healing composition HYALUZINC®.

Example 3: Healing Treatment of Anal Fissures

For this study, a first line or second line treatment of anal fissures was carried out on 30 subjects with the composition of example 1 compared with a positive control (ointment HEC).

The results obtained after 3 weeks of treatment clearly demonstrate for the product of the invention better healing, including in the second line recidivous fissures. The healing is complete in 80% of the cases.

In all the cases, there is a marked decrease in the associated pain (greater than 80%).

Example 4: Healing Treatment of Mouth Injuries

A study was carried out on 7 cases with the composition of example 1 on persons with aphthae.

The healing power of the composition of the invention allows good resorption of the injuries by 80% and a rapid decrease in the associated pain by 90%.

Example 5: Healing of Labial Herpes Spots

This example relates to a test carried out on 10 volunteers with labial herpes (cold sore) by local application of the composition of example 1.

The results observed are a deflation of the blister, within a few hours after the first application, and following several applications a gradual stopping of the inflammation and a rapid subsequent healing (2 to 5 days depending on the size of the lesion).

Example 6: Nasal Decongestant

Study carried out on 25 persons having symptoms of "blocked nose" in an equivalent manner on both sides.

The composition of the invention is locally applied and spread over the left nasal cavity, the right nasal cavity serving as a control.

The result is an immediate decongestant effect on the treated nostril compared with the untreated nostril (greater than 90%). This state lasts depending on the condition for at least 20 to 30 minutes. The operation is then repeated with the same result. Furthermore, a decrease in reddening and in pain (greater than 80%) is observed in parallel on the treated side.

Example 7: Healing of Wasp, Horsefly and Jellyfish Stings

A study was carried out on 5 cases of jellyfish stings, 5 cases of horsefly stings and 10 cases of wasp stings.

In the case of the horseflies and the wasps, in 100% of the cases, the pain disappeared between 1 to 3 minutes maximum. There was no inflammation or reddening and the sting mark disappeared within a few hours.

As regards the stings of jellyfish of the *Pelagianoctiluca* type, a very urticant Mediterranean species, if the composition were applied less than 2 minutes after the sting, the pain disappeared between 5 and 10 minutes.

The inflammation is minimal and the sting marks do not last for more than 48 hours in all the stinging cases.

Example 8: Healing Treatment of Seborrheic Dermatitis of the Face

This study was carried out with 15 volunteers with seborrheic dermatitis of the face over 4 weeks.

The composition of example 1 was applied in the form of a hydrogel. This gel statistically significantly reduced the inflammatory lesions (−26%), it made it possible to cool and remoisturize the epidermis, allowed tightening of the distended pores (−15%) and a decrease in the comedones (−18%). A decrease was observed in the reddening associated with good healing of the lesions with the disappearance of the yellowish scales and scabs.

Example 9: Healing and Soothing Treatment of Eczema and Psoriatic Conditions

A study was carried out on 10 cases with eczema and on 5 cases with psoriatic conditions by applying the composition of example 1 for a period of four weeks.

The pain and oozing decreased by 90% after 4 to 6 applications. In both types of condition, it is possible to note the 80% decrease in reddening after ten days of treatment.

Here again, the healing and soothing effect after local application of a composition according to the invention in order to combat an eczema or a psoriatic condition proved particularly effective.

Example 10: Healing Treatment of Diaper Rashes in Children and Adults

A study on 23 cases clearly demonstrated the favorable results of the composition of the invention. Indeed, after 12 to 48 hours depending on the extent of the erythema, the latter disappeared by nearly 95%. It was always accompanied by good healing and a disappearance of the pain.

The invention claimed is:

1. A hydrogel composition for topical application to acute or chronic wounds or lesions of skin or mucosa affecting the dermis, consisting of:
   water,
   0.5-1.5% by weight of 1,2-octanediol,
   5-25% by weight of glycerol,
   1-5% by weight of polyethylene glycol having a molecular mass of the order of 400 g/mol, and
   0.01-2% by weight of at least one poly(meth)acrylate polymer,
   wherein the percentages by weight are expressed relative to the total weight of the composition.

2. The composition as claimed in claim 1, wherein the lesions of skin or mucosa are oozing lesions, and produce liquids such as lymph, blood or pus.

3. The composition as claimed in claim 1, wherein the composition absorbs liquids such as lymph, blood or pus that are produced by the lesions.

4. The composition as claimed in claim 1, wherein said composition comprises at least two poly(meth)acrylate polymers.

5. The composition as claimed in claim 1, wherein 1,2-octanediol, glycerol, polyethylene glycol, and poly(meth)acrylate polymer are provided in a sufficient amount to induce at least one effect selected from the group consisting of avoiding infection, limiting loss of tissue by necrosis, limiting oozing, controlling edema, and relieving pain.

* * * * *